US007348180B2

(12) United States Patent
Liberman

(10) Patent No.: US 7,348,180 B2
(45) Date of Patent: Mar. 25, 2008

(54) METHOD OF EVALUATING FRESHNESS OF A FISH PRODUCT

(75) Inventor: Barnet Liberman, New York, NY (US)

(73) Assignee: Winterlab Limited, New York, NY (US)

( * ) Notice: Subject to any disclaimer, the term of this patent is extended or adjusted under 35 U.S.C. 154(b) by 32 days.

(21) Appl. No.: 11/078,040

(22) Filed: Mar. 11, 2005

(65) Prior Publication Data

US 2005/0272157 A1 Dec. 8, 2005

Related U.S. Application Data

(60) Provisional application No. 60/553,059, filed on Mar. 15, 2004, provisional application No. 60/552,778, filed on Mar. 12, 2004.

(51) Int. Cl.
*G01N 33/04* (2006.01)
*G01N 33/08* (2006.01)
*G01N 21/64* (2006.01)
*G01N 21/66* (2006.01)
*B32B 5/02* (2006.01)
*B32B 27/04* (2006.01)
*B32B 27/12* (2006.01)

(52) U.S. Cl. ................. 436/21; 436/63; 422/82.08
(58) Field of Classification Search .............. None
See application file for complete search history.

(56) References Cited

U.S. PATENT DOCUMENTS 4,309,185 A * 1/1982 Simon et al. ............. 436/21
5,314,805 A * 5/1994 Haugland et al. ........... 435/29
5,744,321 A 4/1998 Harewood
6,428,980 B1 * 8/2002 Luo et al. ............... 435/69.1
2004/0132166 A1* 7/2004 Miller et al. ............. 435/286.1
2004/0185447 A1 9/2004 Maples et al.

OTHER PUBLICATIONS

Wikipedia, Trypan Blue, last viewed on Sep. 28, 2007, available at http://en.wikipedia.org/w/index.php?title=Trypan_blue.*
Invitrogen Catalog No. Y3601, YOYO-1, last viewed on Sep. 28, 2007, available at https://catalog.invitrogen.com/index.cfm?fuseaction=viewCatalog.viewProductDetails&sku=&productDescription=3846&ref=http%3A%2F%2Fprobes%2Einvitrogen%2Ecom%2Fhandbook%2Ftables%2F0380%2Ehtml.*
Invitrogen Catalog No. S7020, SYTOX Green, last viewed on Sep. 28, 2007, available at https://catalog.invitrogen.com/index.cfm?fuseaction=viewCatalog.viewProductDetails&sku=&productDescription=3814&ref=http%3A%2F%2Fprobes%2Einvitrogen%2Ecom%2Fhandbook%2Ftables%2F0380%2Ehtml.*
Modular Probes Live/Dead Viability/Cytotoxicity Kit, (L-3224) Revised: Jan. 24, 2001.

* cited by examiner

*Primary Examiner*—Jill Warden
*Assistant Examiner*—Keri A Moss
(74) *Attorney, Agent, or Firm*—Cohen Pontani Lieberman & Pavane LLP

(57) ABSTRACT

A method of evaluating freshness of a fish product by cutting a small quantity of sample from the fish product, adding an effective amount of a staining reagent containing at least one of a cell-permeant dye and a cell-impermeant fluorescent dye onto the sample, incubating the sample for a predetermined duration, and determining the freshness of the fish product based on the fluorescence emitted from the sample.

33 Claims, 10 Drawing Sheets
(6 of 10 Drawing Sheet(s) Filed in Color)

METHOD OF EVALUATING FRESHNESS OF A FISH PRODUCT

RELATED APPLICATIONS

This patent application claims the priority of Provisional Application No. 60/552,778 filed on Mar. 12, 2004 and Provisional Application No. 60/553,059 filed on Mar. 15, 2004, the entire disclosure content of which are hereby explicitly incorporated by reference.

BACKGROUND OF THE INVENTION

1. Field of the Invention

The present invention relates to the detection and evaluation of the freshness or the extent of degradation or spoilage of a protein based product, as an indication of the degree of the quality of the protein based product.

2. Description of the Related Art

Traditional methods for evaluating the freshness or degree of spoilage of fish include sensory evaluation (appearance, feel, and smell). This method is subjective and debatable.

U.S. Pat. No. 5,744,321 discloses a colorimetric method for rapidly evaluating the degree of bacterial degradation of fish, such as codfish, catfish, and winter flounder, by mixing the fish flesh with a bacterial nutrient broth, and reacting the extract with a water-soluble chromogen such as an ionized tetrazolium dye salt which undergoes a reduction reaction with the fish bacteria to produce a water-insoluble formazan dye or colored reaction product. Next, a surface active agent is added to help solubilize the formed formazan dye, and produce lysis and stop the reaction, and an aliphatic alcohol solvent is added to dissolve the formed formazan dye or colored reaction product, and prevent further breakdown and darkening with time. The dissolved reaction product has a color which is intensified depending upon the bacterial population of the fish sample and which can be evaluated calorimetrically by visual comparison with a standard color chart indicative of low, medium and high bacterial populations. This method is complicated because it involves quite a few steps and reagents.

Therefore, there is still a need to provide an accurate, convenient, and objective method of evaluating the freshness of a fish product for fish purveyors, restaurants, hospitality companies, and food service companies, etc.

SUMMARY OF THE INVENTION

The present invention provides a method of evaluating freshness of a fish product comprising:

cutting a small quantity of sample from the fish product;

adding an effective amount of a staining reagent comprising at least one of a cell-permeant dye and a cell-impermeant fluorescent dye onto the sample;

incubating the sample added with the staining reagent for a predetermined duration; and determining the freshness of the fish product based on at least one of the following parameters: the intensity of a first fluorescence emitted from the incubated sample, the intensity of a second fluorescence emitted from the incubated sample, a first distance starting from the top of the sample to the farthest point in the sample at which the first fluorescence is detected, and a second distance starting from the top of the sample to the farthest point in the sample at which the second fluorescence is detected.

In the presence of intracellular esterase activity, the cell-permeant dye converts to a compound emitting the first fluorescence. The cell-impermeant fluorescent dye does not cross intact membranes of live cells but can penetrate into compromised membranes of cells and emit the second fluorescence. When the staining reagent comprises both of the cell-permeant dye and the cell-impermeant dye, the first fluorescence should be distinguished from the second fluorescence, i.e. they emit different fluorescent colors. Examples of the cell-permeant dye include calcein acetoxymethylester (hereinafter "calcein AM"), and dodecylresazurin (hereinafter "C12-resazurin"). Examples of the cell-impermeant dye include ethidium homodimer-1 (hereinafter EthD-1 homodimer), SYTOX® Green dye, and YOYO-1® dye. SYTO® Green dye is a cyanine cell-impermeable dye that fluoresces bright green when bound nucleic acid. YOYO-1® dye is a cell-impermeable dye that fluoresces bright green when bound to DNA.

In addition, the cell-permeant dye such as calcein AM and C12-resazurin may be used in combination with Trypan Blue dye, which is a diazo dye used to selectively color dead tissues or blue. Trypan Blue dye staining depends on loss of membrane integrity in dead cells. Trypan Blue dye is normally excluded by intact cell membranes. In general, when the cells are dead, they are permeable to Trypan Blue dye. Thus, Trypan Blue dye can quench the fluorescence of dead cells in conjunction with the cell-permeant dye. The reduction of fluorescence after adding Trypan Blue can be a measure of dead cells.

In accordance with one embodiment of the present invention, the step of determining can be conducted by comparing the at least one parameter with a pre-established correlation between the freshness and the at least one parameter.

The intensities of the first fluorescence and the second fluorescence can be quantified by a digital device, and the pre-established correlation can be established based on the quantified intensities of the first fluorescence and the second fluorescence.

In accordance with another embodiment of the present invention, the first fluorescence and the second fluorescence can be recorded in an image by an optical device, and the pre-established correlation between the freshness and the intensity of the at least one of the first fluorescence and the second fluorescence can be illustrated in a standard color chart.

Preferably, the staining reagent comprises an effective amount of calcein AM and an effective amount of EthD-1 homdimer. The freshness of the first product then can be determined based on the red (EthD-1 homdimer) fluorescence and the green (calcein) fluorescence emitted from the sample.

In accordance with yet another embodiment of the present invention, the cell-impermeant fluorescent dye contained in the staining reagent is Tryan Blue dye. The freshness of the first product then can be determined based on the blue color appearing on the sample. Preferably, the freshness is determined based on the distance that the Trypan Blue dye penetrates into the sample where a fresher fish corresponds to a shorter penetration distance.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings.

DETAILED DESCRIPTION OF THE PRESENTLY PREFERRED EMBODIMENTS

Experimental Material and Procedure

Salmon Filet

Two packages of frozen salmon filet in good condition were cleaved into 8 portions. Each portion is about 60 grams while still frozen. Four portions were placed in a cold room with a continuous temperature of 1° C. (+/−0.5° C.), the other four portions were placed in a standard laboratory refrigerator maintained at 4° C. All these portions were stored in a re-sealable bag to prevent oxidation and dehydration when not being sampled.

Sampling Methods

Figure 1:
FIG. 1 shows the sampling tube used in the example.

Samples of the salmon filet were collected daily and observed for changes. For accurate measurements, consistent sample size is important. A tool for sampling was made to bore a sample from the fish. The tool used in the experiments was a clear Lexan® (polycarbonate resin) tube having 4.8 mm of external diameter, 2.1 mm of internal diameter, and 90 mm of length. One end of the tube was beveled to form a cutting surface (see FIG. 1). When inserted into the flesh of a fish product, a part of flesh is pressed into the bottom opening of the tube. Then by gently twisting and lifting, a sample is removed and remains in the tube. An applicator with 2 mm external diameter may be used to gently tap the sample and remove any air space. The tube is preferably designed with food safe qualities and is optically clear. Other acrylics or polycarbonate materials may also be suitable. Thus, the sample obtained by such a tool has a size of about 2.1 mm×~5 to 25 mm.

This sampling gives several advantages, including:

Small, reproducible sample size

Standard sample size

Neat labeling container

Inexpensive, disposable, nontoxic tool

Unbreakable

Sample viewable through tube

Staining, Incubating

A small volume of staining solution can be added into the top opening of the tube and incubated for an appropriate period of time, e.g., about 10 minutes. Typically, the volume of the staining solution may range from 1 µl to 1 ml. The incubating time may range from 1 minute to 1 hour.

The staining solution can be a solution containing calcein AM and ethidium homodimer, e.g., the solution made from Molecular Probes' LIVE/DEAD Viability/Cytotoxicity Kit (L3224). The L3224 Kit comprises two probes: calcein AM and ethidium homodimer-1. Calcein AM is a fluorogenic esterase substrate that is hydrolyzed to a green-fluorescent product (calcein). Thus, green fluorescence is an indicator of cells that have esterase activity as well as an intact membrane to retain the esterase products. Green fluorescence means they are alive based on some level of esterase activity. Ethidium homodimer-1 is a high-affinity, red-fluorescent nucleic acid stain that is only able to pass through the compromised membranes of dead cells. When they are red, they are "dead." The concentration of calcein AM may range from 0.1 to 50 µM. The concentration of EthD-1 homodimer range from 0.1 to 100 µM.

The LIVE/DEAD viability/cytotoxicity assay offers several advantages:

Simplicity. The reagents are simultaneously added to the sample, which is then incubated for 3-10 minutes during or immediately following thawing. No wash steps are required before analysis.

Specificity and reliability. Green-fluorescent cells are live; red-fluorescent cells are dead.

Versatility. The LIVE/DEAD viability/cytotoxicity assay is compatible with adherent cells such as astrocytes, nonadherent cells and certain tissues. Results can be analyzed by fluorescence microscopy using standard fluorescein longpass filter sets, as well as by flow cytometry or fluorometry. The fluorescence emissions of the two probes are easily resolved and distinguishable. Single or multiple wavelength LEDs can be used to provide a range of excitation light from 360-520 nm. Other illumination sources include: fluorescence bulbs, mixed gas bulbs, hand held UV sources, projections lamps, and lasers.

Simple quantitation. Measurements of individual cells yield only two populations; there are rarely any doubly stained cells. Tissues may have mixed populations of staining in the "middle" stages.

The staining solution can also be Trypan Blue solution. Trypan Blue is used as a calorimetric stain for determining cellular viability. The concentration of Trypan Blue solution may range from 0.1 to 10 mM. In cell biological experiments, Trypan Blue is the most common stain used to distinguish viable cells from nonviable cells. Only non-viable cells absorb the dye, appear blue, and may also appear asymmetrical. Conversely, live, healthy cells appear round and refractile without absorbing the blue-colored dye. The use of this stain, however, is time-sensitive. Viable cells absorb Trypan Blue over time, and can affect counting and viability results. To prevent viable cells from absorbing the stain, and thus appear non-viable, the sample stained with Trypan Blue may be diluted. For example, the Trypan Blue stained samples may be fixed by immersion in 2% glutaraldehyde in 0.1 M phosphate buffer (pH 7.4) and stored for later observation. To minimize non-viable absorption, sampling is preferably finished within 5-30 minutes. In addition, Trypan Blue has a greater affinity for serum proteins than for cellular proteins. For cells with high serum conditions, the background may be too dark. In this case, cells are preferably isolated from the tissue.

Image Viewing and Recording

Reflective fluorescence images can be taken to document any changes that occur to the staining pattern as a result of storage time and temperature.

To quantitate and/or automate the process, imaging devices having image capture, storage, and/or analysis functions, such as CCD or CMOS devices, may be used. These devices include a UVP BioDocit system with digital camera; a Nikon CoolPix 995 digital camera with telephoto lens; a Nikon Eclipse E800 photomicroscope equipped with brightfield, DIC, phase and fluorescence optics; blue and green LED lights and CCD detection system.

In the present study, the samples were viewed using a 4×, 0.13 n.a. plan fluor objective. Digital images were collected using a CoolCam liquid-cooled, three-chip color CCD camera (Cool Camera Company, Decatur, Ga. 30033) and captured to a Pentium IV 3.0 GHz personal computer using Image Pro Plus version 4.5 software (Media Cybernetics, Silver Springs, Md. 20910). Digital images were stored for future printing and analysis using ImageJ or ImagePro Plus. Adobe PhotoShop and Micorsoft PowerPoint applications were used for presentation.

Digital images were collected so that quantitative methods could be derived to compare the color of the stained sample as a function of the cell viability or "freshness". Color of the stained sample and penetration depth of the stains into the sample are important criteria in evaluating the freshness of the sample.

Results

Live/Dead Fluorescent Assay

The staining solution contains 5.0 µM calcein AM and 10.0 µM EthD-1 homodimer. It was prepared from the reagents of Molecular Probes' LIVE/DEAD Viability/Cytotoxicity Kit (L3224). About 10-30 µl of the staining solution was added onto the top of the samples (2.1 mm×~2-10 mm). The freshness of the sample can be determined based on the ratio of the red and green color changes in fluorescent emission after being incubated for about 5-10 minutes. The fluorescence image was obtained by exciting the sample at wavelength of 490±40 nm and collected at 525±20 nm.

Figure 2:
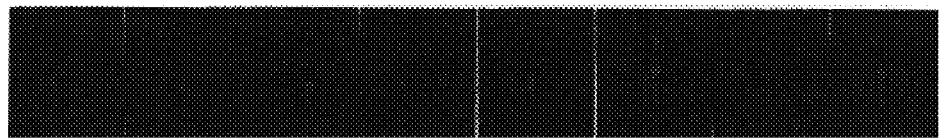
FIG. 2 shows the fluorescent images of salmon samples stored at 1° C. and collected at different storage days by using the Live/Dead fluorescent assay.
Figure 3:
FIG. 3 shows the fluorescent images of the salmon samples stored at 1° C. and collected at storage Day 1 and Day 8 by using the Live/Dead fluorescent assay.

FIGS. 2 and 3 shows the assay results of the salmon samples stored for different days at the same temperature (1° C.). The image as shown in FIG. 2 was taken 5 minutes following the stain addition. Green color indicates esterase activity (fresh). Red color indicates nuclei of cells with compromised membranes. The distance that the stain travels from top to bottom appears to be related to the storage days. The image as shown in FIG. 3 was taken 30 minutes after the staining of the samples.

Figure 4:
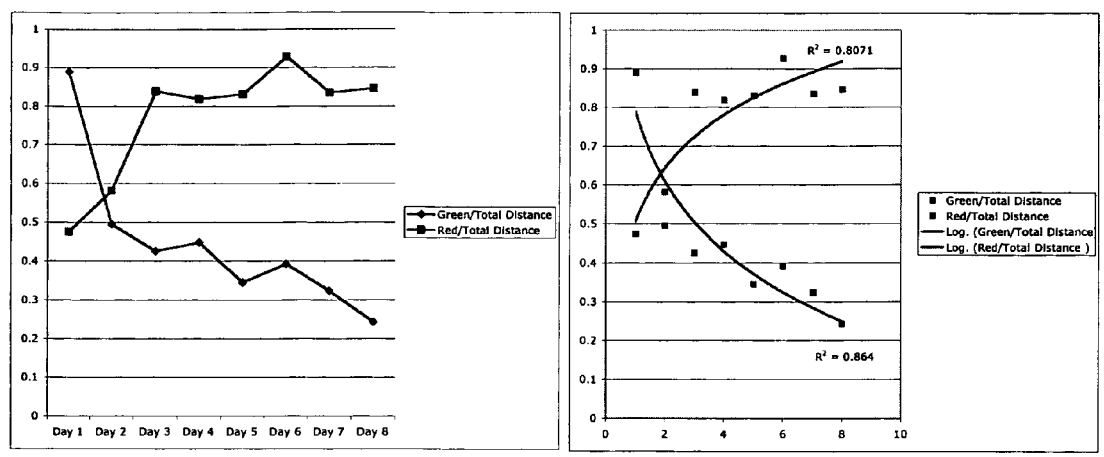
FIG. 4 illustrates the correlation of the freshness of the salmon samples and the ratio of the distance starting from the top of the sample to the farthest point in the sample at which the green fluorescence is detected and the distance starting from the top of the sample to the farthest point in the sample at which the red fluorescence being detected.

The following table shows summary data of fluorescent freshness Live/Dead assay (5.0 µM calcein AM and 10.0 µM of EthD-1 homodimer-1) on frozen salmon sample stored at 1° C. and sampled at 24-hour intervals. FIG. 4 shows the correlation between the freshness of the fish product and the ratio of the distance traveled of green fluorescence and red fluorescence.

TABLE 1

Summary Data of Live/Dead Fluorescence Assay

| Ratio of distance traveled vs. total distance | Day 1 | Day 2 | Day 3 | Day 4 | Day 5 | Day 6 | Day 7 | Day 8 |
|---|---|---|---|---|---|---|---|---|
| Green/Total Distance | 0.89 | 0.49 | 0.42 | 0.44 | 0.34 | 0.39 | 0.32 | 0.24 |
| SD between the days for Green/Total dis. | 0.237 | | | | | | | |
| Red/Total Distance | 0.47 | 0.58 | 0.83 | 0.81 | 0.83 | 0.92 | 0.83 | 0.84 |
| SD between the days for Red/Total dis. | 0.155 | | | | | | | |

Figure 5:
FIG. 5 shows the fluorescent images of the sample collected from a live rainbow trout.
Figure 6:
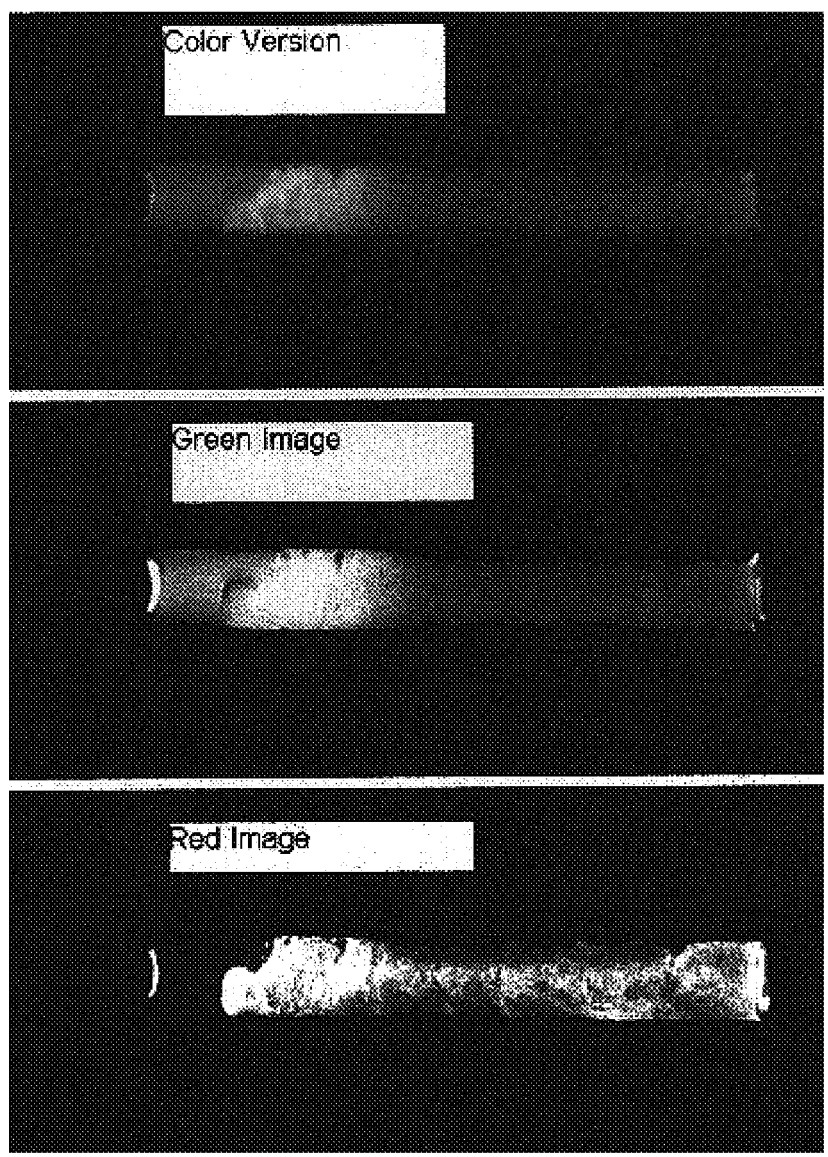
FIG. 6 shows the fluorescent images of the sample collected from a rainbow trout fish product stored at 4° C. for seven days.

FIGS. 5-8 shows the fluorescence assay results of other fish species stored for different days at the same temperature. FIG. 5 shows the fluorescence result of the fresh rainbow trout (Oncorhynchus mykiss) sample. FIG. 6 shows fluorescence result of the rainbow trout sample stored at 4° C. for seven days. In FIG. 6, the top image reflects both green and red information of the samples; the middle image is a grayscale image from the green information; the bottom image is a grayscale image from the red information. Both images of FIGS. 5 and 6 were taken 30 minutes following the stain addition to the rainbow trout sample. Stain was added to the opening in the top (left side of image) of the tube.

Figure 7:
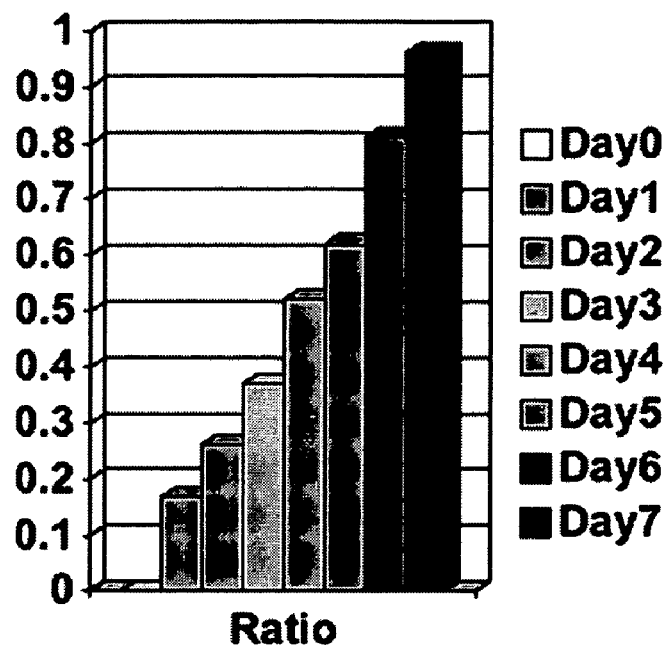
FIG. 7 illustrates correlation between freshness of the rainbow trout sample and the ratio of the distance starting from the top of the sample to the farthest point in the sample at which the green fluorescence is detected and the distance starting from the top of the sample to the farthest point in the sample at which the red fluorescence is detected.

The graph of FIG. 7 is based on the assay results of rainbow trout samples from 3 fish (12 total samples) collected daily from fish stored 7 days at 4° C. The samples were imaged 30 minutes following stain addition. This graph illustrates the mean ratio of the distance traveled of the green and red fluorescence for samples taken at the same day.

Figure 8:
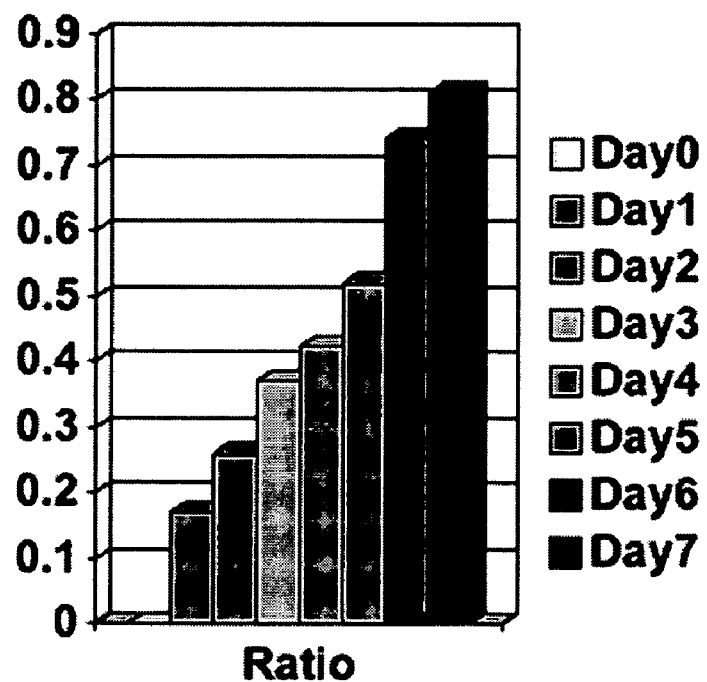
FIG. 8 shows correlation between freshness of a Dover sole sample and the ratio of the distance starting from the top of the sample to the farthest point in the sample at which the green fluorescence is detected and the distance starting from the top of the sample to the farthest point in the sample at which the red fluorescence is detected.

FIG. 8 shows the correlation of the freshness of Dover sole (*Microstomus pacificus*) with the ratio of the distance traveled of the green and red fluorescence. The procedure in connection with FIG. 8 is the same as that of FIG. 7 except that the rainbow trout samples of FIG. 7 were replace with Dover sole (*Microstomus pacificus*).

Figure 9:
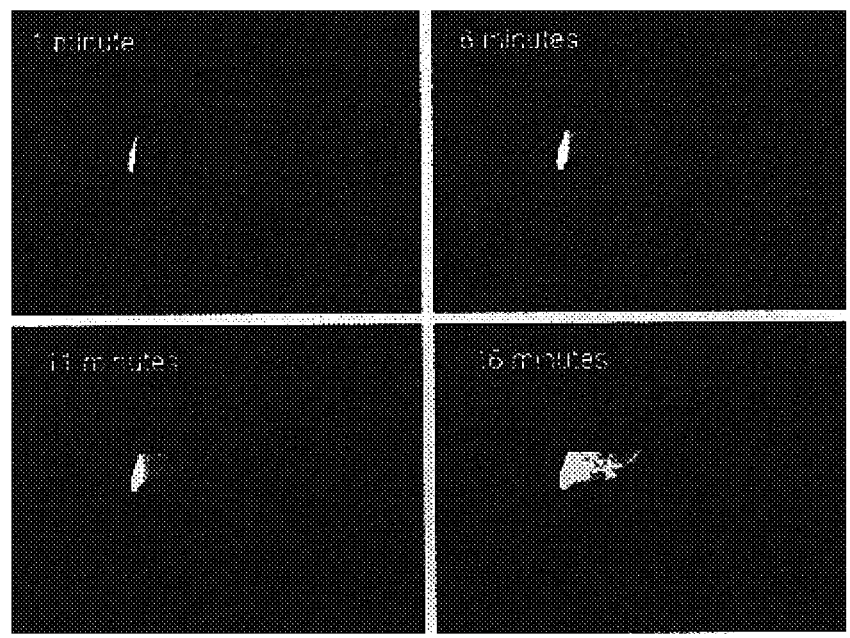
FIG. 9 shows time-lapse images from dye addition to 16 minutes of the Dover sole sample stored at 1° C. for five days by using the Live/Dead fluorescent assay.

The time-lapse images as shown in FIG. 9 demonstrate that the dye uptake changes with time. The sample used is the Dover sole (*Microstomus pacificus*) sample stored for 5 days at 1° C.

Figure 10:
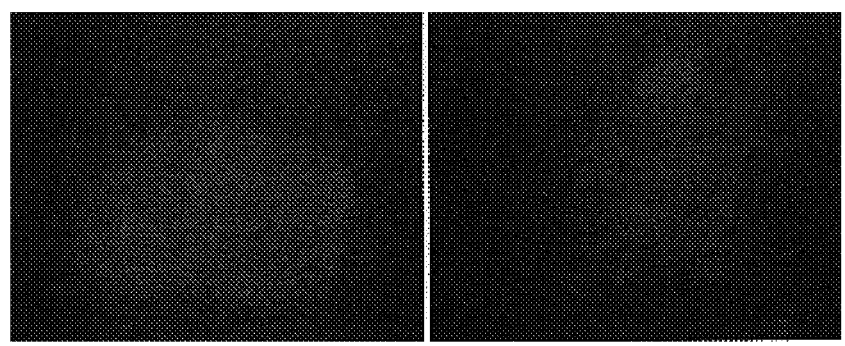
FIG. 10 shows the fluorescent images of the salmon samples stored at 1° C. and collected at storage Day 1 and Day 5.

FIG. 10 shows the fluorescence images of salmon samples placed on plates.

Trypan Blue Measurements

About 10-30 μl Trypan Blue staining reagent (0.5% w/v) was added onto the top of the samples (2.1 mm×2~10 mm). The penetration depth of the Trypan Blue dye into the sample was measured. The incubation time is 10 minutes. The samples had been stored at 1° C. and labeled at room temperature. Trasimifted/reflected light was used to view the samples.

Figure 11:
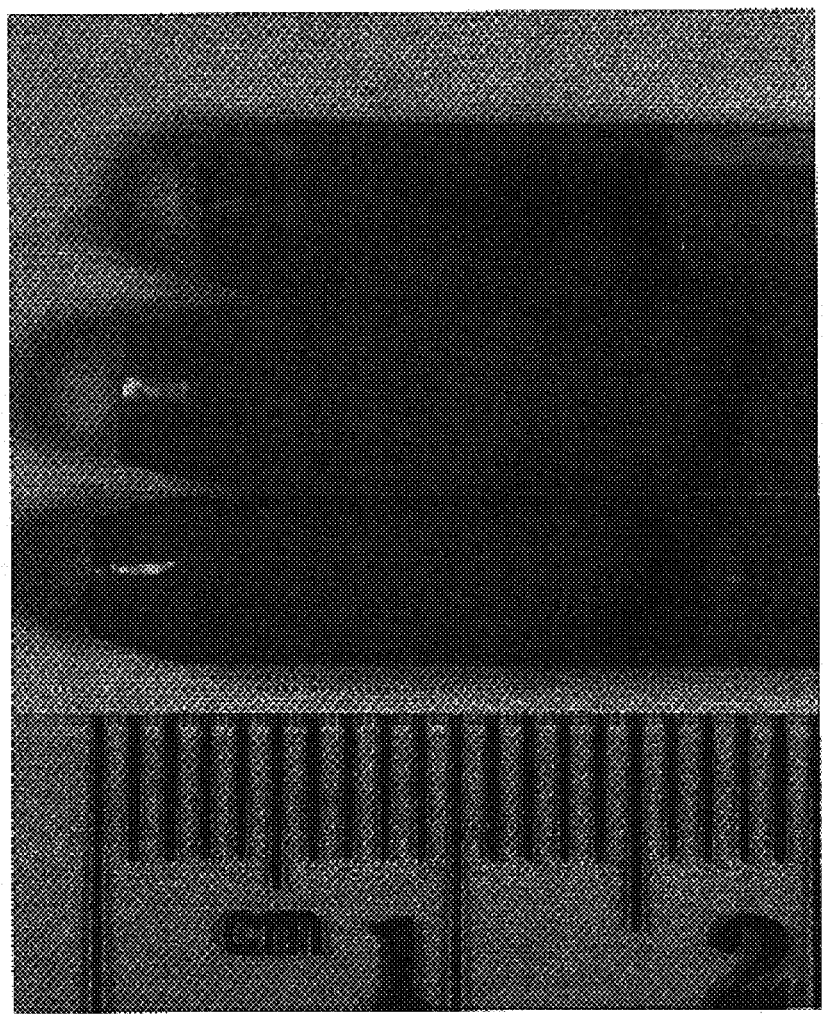
FIG. 11 illustrates the penetration depths of the Trypan Blue staining dye into the salmon samples stored at 1° C. and collected at storage Day 1, Day 4, and Day 7 by using the Trypan Blue assay.
Figure 12:
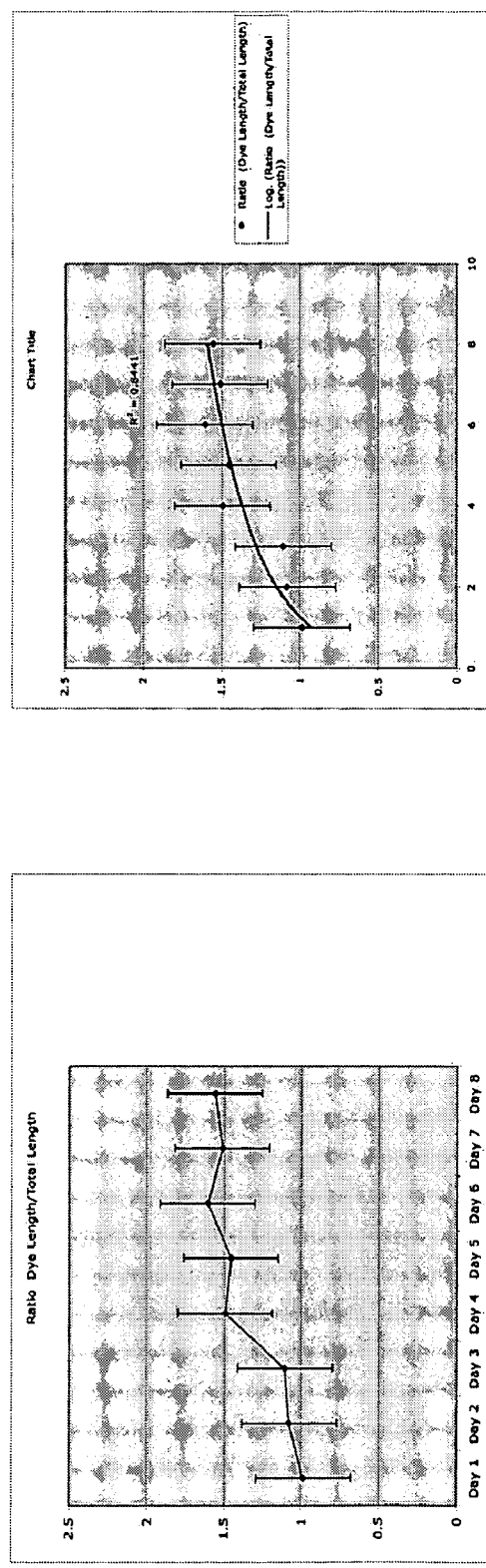
FIG. 12 illustrates the distance that the Trypan Blue dye penetrates into the salmon samples at temperature of 1° C. collected from storage Day 1 to Day 8.

FIGS. 11 and 12 show the correlation of freshness of the salmon samples with the distance that the Trypan blue dye penetrated into the sample. As shown in FIG. 12, Day 1 is unique, Day 2 and Day 3 are similar, Day 4 to Day 8 are similar in the ratio of the penetration distance of the dye to the total length of the sample. Day 1 is significantly different from the rest, and Day 2 and Day 3 are significantly different from Day 4 to Day 8.

The following table lists the summary data of Trypan Blue assay.

TABLE 2

Summary Data of Trypan Blue Assay

| Trypan Blue staining | Day 1 | Day 2 | Day 3 | Day 4 | Day 5 | Day 6 | Day 7 | Day 8 |
|---|---|---|---|---|---|---|---|---|
| Ratio (stain/sample length) | 0.985 | 1.078 | 1.105 | 1.492 | 1.453 | 1.606 | 1.509 | 1.557 |
| Stand Deviation of each day | 0.084 | 0.107 | 0.112 | 0.294 | 0.296 | 0.484 | 0.316 | 0.377 |
| Stand Deviation of the ratio | 0.0245 | | | | | | | |
| Confidence Interval (95%) for all | 0.307 | | | | | | | |
| Confidence Interval for each day = ratio mean of the day + and −1.96*sqrt(0.0245)/sqrt(ni) | | | | | | | | |
| ni | 119 | 106 | 110 | 117 | 143 | 182 | 128 | 170 |
| Confidence Interval for each day | Lower | Upper | | | | | | |
| day 1 | 0.957 | 1.013 | | | | | | |
| day 2 | 1.048 | 1.108 | | | | | | |
| day 3 | 1.076 | 1.134 | | | | | | |
| day 4 | 1.464 | 1.52 | | | | | | |
| day 5 | 1.427 | 1.479 | | | | | | |
| day 6 | 1.583 | 1.629 | | | | | | |
| day 7 | 1.482 | 1.536 | | | | | | |
| day 8 | 1.581 | 1.533 | | | | | | |

The invention is not limited by the embodiments described above which are presented as examples only but can be modified in various ways within the scope of protection defined by the appended patent claims.

I claim:

1. A method of evaluating freshness of a fish product comprising:

cutting a small quantity of sample from the fish product;

adding an effective amount of a staining reagent comprising at least one of a cell-permeant dye and a cell-impermeant fluorescent dye onto the sample; wherein the cell-permeant dye converts to a compound emitting a first fluorescence in the presence of intracellular esterase activity; wherein the cell-impermeant fluorescent dye can penetrate into compromised membranes of cells and emit a second fluorescence; and wherein the first fluorescence and the second fluorescence are distinguishable from each other when the indicator reagent comprises both the cell-permeant dye and the cell-impermeant dye;

incubating the sample added with the staining reagent for a predetermined duration; and determining the freshness of the fish product based on at least one parameter selected from the group consisting of (1) the intensity of the first fluorescence emitted from the incubated sample, (2) the intensity of the second fluorescence emitted from the incubated sample, (3) a first distance starting from the top of the sample to the farthest point in the sample at which the first fluorescence is detected, (4) a second distance starting from the top of the sample to the farthest point in the sample at which the second fluorescence is detected.

2. The method of claim 1 wherein the step of determining is conducted by comparing the at least one parameter with a pre-established correlation between the freshness and the at least one parameter.

3. The method of claim 2 wherein the intensities of the first fluorescence and the second fluorescence are quantified by a digital device, and the pre-established correlation is established based on the quantified intensities of the first fluorescence and the second fluorescence.

4. The method of claim 3 wherein the intensities of the first fluorescence and the second fluorescence are recorded in an image by an optical device, and the pre-established correlation between the freshness and the intensity of the at least one of the first fluorescence and the second fluorescence is illustrated in a standard color chart.

5. The method of claim 1 wherein the staining reagent comprises both the cell-permeant dye and the cell-impermeant dye.

6. The method of claim 5 wherein the determining of the freshness of the fish product is based on the ratio of the intensities of the first fluorescence and the second fluorescence.

7. The method of claim 5 wherein the determining of the freshness of the fish product is based on the ratio of the first distance and the second distance.

8. The method of claim 5 wherein the cell-permeant dye is calcein acetoxymethylester. and the cell impermeant dye is ethidium homodimer-1, whereby the first fluorescence is green, and the second fluorescence is red.

9. The method of claim 5 wherein the cell permeant dye dodecylresazurin. and the cell-impermeant dye is a cyanine cell-impermeable dye that fluoresces bright green when bound to nucleic acid, whereby the first fluorescence is red, and the second fluorescence is green.

10. The method of claim 1 wherein the cell-permeant dye is selected from the group consisting of calcein acetoxymethylester and dodecylresazurin, and the cell-impermeant dye is selected from the group consisting ethidium homodimer-1, a cell-impermeable dye that fluoresces briight green when bound to DNA, and a cyanine cell-impermeable dye that fluoresces bright green when bound to nucleic acid.

11. The method of claim 1 wherein the staining reagent further comprises a diazo dye used to selectively color dead tissues or dead cells blue dye when the staining reagent comprises the cell-permeant dye.

12. A method of evaluating freshness of a fish product comprising:
cutting a small quantity of sample from the fish product;
adding a staining reagent comprising an effective amount of calcein acetoxymethylester and an effective amount of ethidium homodimer-1 onto the sample;
incubating the sample added with the staining reagent for a predetermined duration;
determining the freshness of the fish product based on, at least one of (a) the intensity of a green fluorescence and (b) a first distance starting from the top of the incubated sample to the farthest point in the incubated sample at which the green fluorescence being detected; and at least one (c) of the intensity of a red fluorescence and (d) a second distance starting from the top of the incubated sample to the farthest point in the incubated sample at which the red fluorescence being detected.

13. The method of claim 12 wherein the determining of the freshness is based on the ratio of the intensities of the green fluorescence and the red fluorescence.

14. The method of claim 12 wherein the determining of the freshness is based on the ratio of the first distance and the second distance.

15. The method of claim 12 wherein the determining of the freshness is conducted by comparing the intensities of the green fluorescence and the red fluorescence with pre-established correlation between the freshness and the intensities of the green fluorescence and the red fluorescence.

16. The method of claim 15 wherein the intensities of the green fluorescence and the red fluorescence are quantified by a digital device, and the pre-established correlation is established based on the quantified intensities of the green fluorescence and the red fluorescence.

17. The method of claim 15 wherein the intensities of the green fluorescence and the red fluorescence are recorded in an image by an optical device, and the pre-established correlation between the freshness and the intensities of the green fluorescence and the red fluorescence is illustrated in a standard color chart.

18. The method of claim 12 wherein the staining reagent comprises 0.1-50 µM calcein acetoxymethylester.

19. The method of claim 12 wherein the staining reagent comprises 0.1-100 µM ethidium homodimer-1.

20. The method of claim 12 wherein the amount of the staining reagent is from about 1 µL to 1 mL.

21. The method of claim 12 wherein the predetermined duration of the incubating step is from about 1 to 45 minutes.

22. The method of claim 12 wherein the predetermined duration of the incubating step is from about 5 to 10 minutes, and the incubating step is conducted at room temperature.

23. The method of claim 12 wherein the fish product is selected from the group consisting of salmon, rainbow trout, Dover sole, and halibut.

24. A method of evaluating freshness of a fish product comprising:
cutting a small quantity of sample from the fish product;
adding a staining reagent comprising an effective amount of a diazo dye used to selectively color dead tissues or dead cells blue dye onto the sample;
incubating the sample added with the staining reagent for a predetermined duration;
determining the freshness of the fish product based on a penetration distance starting from the top of the incubated sample to the farthest point in the incubated sample at which the blue fluorescence is detected.

25. The method of claim 24 wherein the determining of freshness is conducted by comparing the penetration distance with a pre-established correlation between the freshness and the penetration distance.

26. The method of claim 24 wherein the staining reagent comprises 0.1-10 mM of the a diazo dye used to selectively color dead tissues or dead cells blue dye.

27. The method of claim 24 wherein the amount of the staining agent is from 1 µL to 1 mL.

28. The method of claim 24 wherein the predetermined period of time of the incubating step is from about to 2 minutes and 45 minutes.

29. The method of claim 24 wherein the predetermined period of time of the incubating step is from about 10-30 minutes, and the incubating is conducted at room temperature.

30. A method of evaluating freshness of a fish product comprising:
cutting a small quantity of sample from the fish product;
placing the sample into a tube;
adding an effective amount of a staining reagent comprising at least one of a cell-permeant dye and a cell-impermeant fluorescent dye onto the sample in the tube; wherein the cell-permeant dye converts to a compound emitting a first fluorescence in the presence of intracellular esterase activity; wherein the cell-impermeant fluorescent dye can penetrate into compromised membranes of cells and emit a second fluorescence; and wherein the first fluorescence and the second fluorescence are distinguishable from each other when the staining reagent comprises both the cell-permeant dye and the cell-impermeant dye;
incubating the sample added with the staining reagent for a predetermined duration; and
determining the freshness of the fish product based on at least one parameter selected from the group consisting of (1) a first ratio of a first distance starting from the top of the sample to the farthest point in the sample, at which the first fluorescence is detected, and the total length of the sample in the tube, and (2) a second ratio of a second distance starting from the top of the sample to the farthest point in the sample, at which the second fluorescence is detected, and the total length of the sample in the tube.

31. The method of claim 30 wherein the sample has a size of about 2.1 mm in diameter and about 5 to 25 mm in length.

32. The method of claim 30 wherein the sample has a size of about 2.1 mm in diameter and about 2 to 10 mm in length, the staining reagent is a solution comprising 5 µM calcein acetoxymethylester, 10 µM ethidium homodimer-1, and the amount of solution is about 10-30 µL.

33. The method of claim 30 wherein the predetermined duration of the incubating step is from about 3 to 10 minutes, and the incubating step is conducted at room temperature.

* * * * *